(12) United States Patent
Cynshi

(10) Patent No.: US 6,417,225 B1
(45) Date of Patent: Jul. 9, 2002

(54) PROPHYLACTIC/THERAPEUTIC AGENTS FOR ATHEROSCLEROSIS

(75) Inventor: Osamu Cynshi, Shizuoka-ken (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/606,682

(22) Filed: Jun. 30, 2000

Related U.S. Application Data

(62) Division of application No. 09/423,365, filed as application No. PCT/JP98/01861 on Apr. 23, 1998, now Pat. No. 6,156,793.

(30) Foreign Application Priority Data

May 8, 1997 (JP) ............................................. 9-154260

(51) Int. Cl.$^7$ ............................................. A61K 31/352
(52) U.S. Cl. ........................................ 514/462; 514/469
(58) Field of Search ................................. 514/462, 469

(56) References Cited

U.S. PATENT DOCUMENTS 5,574,178 A * 11/1996 Tamura et al. ............... 549/462

FOREIGN PATENT DOCUMENTS

JP 8-125579 * 5/1996

* cited by examiner

*Primary Examiner*—Fiona T. Powers
(74) *Attorney, Agent, or Firm*—Browdy and Neimark

(57) ABSTRACT

Herein disclosed are prophylactic/therapeutic agents for atherosclerosis containing a compound of general formula (1):

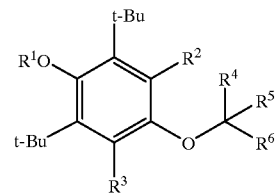

(1)

wherein $R^1$ represents a hydrogen atom or an acyl group, $R^2$ represents a lower alkyl group, $R^3$ represents a hydrogen atom or a lower alkyl group, and $R^4$, $R^5$ and $R^6$ represent a hydrogen atom, an alkyl group, an alkenyl group, an alkynyl group or an aryl group, or $R^2$ and $R^4$ together with the oxygen atom may form a furan or dihydrofuran ring, or $R^5$ and $R^6$ may combine to form a cycloalkyl group or a heterosubstituted cycloalkyl group in which one or more methylene groups of the cycloalkyl group are replaced by oxygen, sulfur or alkyl-substituted nitrogen atoms, a possible optically active isomer or a pharmaceutically acceptable salt thereof, as an active ingredient.

8 Claims, No Drawings

PROPHYLACTIC/THERAPEUTIC AGENTS FOR ATHEROSCLEROSIS

This is a division of copending parent application Ser. No. 09/423,365, nationalized Nov. 8, 1999 now U.S. Pat. No. 6,156,793, the international application PCT/JP98/01861 of which was filed Apr. 23, 1998.

FIELD OF THE INVENTION

The present invention relates to prophylactic/therapeutic agents for atherosclerosis or xanthomatosis, more specifically, prophylactic/therapeutic agents for atherosclerosis or xanthomatosis containing a 2,6-di-t-butylphenol derivative as an active ingredient.

PRIOR ART

Oxidative denaturation of low-density lipoprotein (LDL) has been known as one of important causes of the development and progress of atherosclerosis and xanthomatosis (Steinberg, D., Parthasarathy, S., Carew, T. E., Khoo, J. C. & Witztum, J. L. Beyond Cholesterol; Modifications of low-density lipoprotein that increase its atherogenicity. N. Engl. J. Med. 320; 915–924, 1989). However, reports have shown that probucol which is an antioxidant has no therapeutic effect on atherosclerosis in clinical tests (Walldius, G., Erikson, U., Olsson, A., Bergstrand, L., Hadell, K., Johansson, J., Kaijser, L., Lassvik, C., Molgaard, J., Nilsson, S., Elinder, L. S., Stenport, G. & Holme, I. The effect of probucol on femoral atheroscleroses: the Probucol Quantitative Regression Swedish Trial (PQRST). Am. J. Cardiol. 84, 875–883, 1994).

As to therapy of arteriosclerosis, HMGCoA reductase inhibitor which is an antihyperlipidemic agent has so far been reported to inhibit the progress of arteriosclerosis (Scandinavian Simvastatin Survival Study Group Randomised trial of cholesterol lowering in 4444 patients with coronary heart disease: the Scandinavian Simvastatin Survival Study (4S). Lancet 344, 1383–1389, 1994). However, patients to be treated with the antihyperlipidemic agent are limited to hyperlipidemic patients, and the antihyperlipidemic agent is ineffective for arteriosclerosis in the patients with familial hyperlipidemia. An antihyperlipidemic agent is considered to reduce the amount of LDL exposed to oxidative modification, thus showing an antiarteriosclerotic effect.

On the other hand, antioxidants capable of directly preventing oxidation of LDL are expected as prophylactic/therapeutic agents for atherosclerosis, but any drugs including the above-mentioned probucol have not been found to have a clinically sufficient effect as a prophylactic/therapeutic agent for atherosclerosis at present.

An object of the present invention is to provide a novel prophylactic/therapeutic agent for atherosclerosis having a clinically sufficient effect.

DISCLOSURE OF THE INVENTION

As a result of extensive research to solve the above problems, we found that compounds of general formula (1):

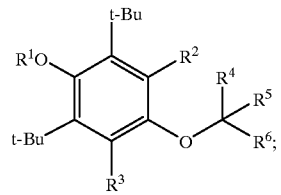

(1)

wherein
$R^1$ represents a hydrogen atom, an acyl group or an arylalkoxycarbonyl group,
$R^2$ represents a lower alkyl group,
$R^3$ represents a hydrogen atom or a lower alkyl group, and
$R^4$, $R^5$ and $R^6$ may be identical or different and each represent a hydrogen atom, an optionally substituted alkyl group, an optionally substituted alkenyl group, an optionally substituted alkynyl group, an optionally substituted aryl group or an optionally substituted arylalkyl group, or
$R^2$ and $R^4$ together with the oxygen atom may form a furan or dihydrofuran ring, or
$R^5$ and $R^6$ may combine to form a cycloalkyl group or a heterosubstituted cycloalkyl group in which one or more methylene groups of the cycloalkyl group are replaced by oxygen, sulfur or alkyl-substituted nitrogen atoms, provided that $R_6$ is absent when $R^2$ and $R^4$ together with the oxygen atom form a furan ring have a potent inhibitory effect against atherosclerosis in rabbit atherosclerosis models and murine atherosclerosis models as well as a potent inhibitory effect against xanthomas in murine xanthoma models.

Compounds of general formula (1) have been shown in JPA No. 6-206842/94. The publication contains the antioxidative data of the compounds demonstrating that they are useful as therapeutic agents for atherosclerosis, myocardial infarction and other diseases as well as that they are effective as antioxidants for ischemic organ disorders such as atherosclerosis, myocardial infarction, cerebral apoplexy, etc., but does not contain any test examples in which models are employed.

MOST PREFERRED EMBODIMENTS OF THE INVENTION

For the definition of $R^1$ in general formula (1), the acyl group preferably contains 1 to 10 carbon atoms, the examples of which include acetyl, formyl, propionyl and benzoyl groups. The arylalkoxycarbonyl group preferably contains 7 to 11 carbon atoms, the examples of which include a benzyloxycarbonyl group.

$R^1$ is preferably a hydrogen atom or an acyl group, more preferably a hydrogen atom. When $R^1$ is an acyl group, it is preferably an acetyl group.

The lower alkyl group for $R^2$ and $R^3$ means a straight or branched alkyl group containing 1 to 6 carbon atoms, the examples of which include methyl, ethyl, n-propyl, i-propyl, n-butyl, s-butyl and t-butyl group.

$R^3$ is preferably a hydrogen atom.

The alkyl group for $R^4$, $R^5$ and $R^6$ means a straight or branched alkyl group preferably containing 1 to 20, more preferably 1 to 10 carbon atoms, the examples of which include methyl, ethyl, n-propyl, i-propyl, n-butyl, s-butyl, t-butyl, pentyl, i-amyl, hexyl, heptyl, octyl, nonyl and decyl groups. The alkenyl group means a straight or branched alkenyl group preferably containing 2 to 20, more preferably 2 to 10 carbon atoms, the examples of which include vinyl, allyl, butenyl, pentenyl, geranyl and farnesyl groups. The alkynyl group means a straight or branched alkynyl group containing 2 to 20, preferably 2 to 10 carbon atoms, the examples of which include ethynyl, propynyl and butynyl groups. The aryl group preferably contains 6 to 20, more preferably 6 to 10 carbon atoms, the examples of which include phenyl, tolyl, xylyl, biphenyl, naphthyl, anthryl and phenanthryl groups. The arylalkyl group means an alkyl group having an aromatic hydrocarbon substituted for a hydrogen atom on the alkyl group, preferably containing 7 to 20, preferably 7 to 11 carbon atoms, the examples of which include benzyl and phenethyl groups.

The above-mentioned alkyl, alkenyl, alkynyl, aryl and arylalkyl groups may have one or more substituents selected from halogen atoms, lower alkyl, lower alkoxy, aryloxy containing 6 to 10 carbon atoms, hydroxy, amino, nitro and/or trifluoromethyl groups. Specifically, halogen atoms include chlorine, bromine, iodine and fluorine; lower alkyl groups include methyl, ethyl, n-propyl, i-propyl, n-butyl, s-butyl and t-butyl groups; alkoxy groups include methoxy, ethoxy, n-propoxy, i-propoxy, n-butoxy, s-butoxy and t-butoxy groups; and aryloxy groups include phenoxy, 3,5-di-t-butyl-4-hydroxy-2-methylphenoxy and naphthoxy groups.

Preferably, $R^2$ and $R^4$ together with the oxygen atom may form a furan or dihydrofuran ring, which is fused with the benzene ring of general formula (1) to form a benzofuran or dihydrobenzofuran ring, respectively. More preferably, $R^2$ and $R^4$ together with the oxygen atom form a dihydrofuran ring, and $R^6$ is absent when $R^2$ and $R^4$ together with the oxygen atom form a furan ring.

The cycloalkyl group formed by $R^5$ and $R^6$ is preferably a cycloalkyl group containing 3 to 8 carbon atoms, the examples of which include cyclopropyl, cyclobutyl, cyclopentyl, cyclohexyl, cycloheptyl and cyclooctyl groups. The examples of the heterosubstituted cycloalkyl group in which one or more methylene groups of the cycloalkyl group are replaced by oxygen, sulfur or C1–6 alkyl-substituted nitrogen atoms includes, for example, tetrahydrothiopyranyl, N-methylpiperidyl and tetrahydropyranyl groups. A heterosubstistituted cycloalkyl group containing one or more oxygen atoms is preferred, and a tetrahydropyranyl group is especially preferred.

Especially preferred compounds of general formula (1) having the above-defined substituents are as follows:
4,6-di-t-butyl-5-hydroxy-2,3-dihydrobenzofuran;
4,6-di-t-butyl-5-hydroxy-2-methyl-2,3-dihydrobenzofuran;
4,6-di-t-butyl-5-hydroxy-2,2-dimethyl-2,3-dihydrobenzofuran;
4,6-di-t-butyl-2,2-diethyl-5-hydroxy-2,3-dihydrobenzofuran;
4,6-di-t-butyl-2,2-di-n-propyl-5-hydroxy-2,3-dihydrobenzofuran;
4,6-di-t-butyl-2,2-di-n-butyl-5-hydroxy-2,3-dihydrobenzofuran;
4,6-di-t-butyl-5-hydroxy-2-octylbenzofuran;
4,6-di-t-butyl-5-hydroxy-2-octyl-2,3-dihydrobenzofuran;
2,4,6-tri-t-butyl-5-hydroxy-2,3-dihydrobenzofuran;
4,6-di-t-butyl-2,2-di-i-propyl-5-hydroxy-2,3-dihydrobenzofuran;
4,6-di-t-butyl-2,2-diphenyl-5-hydroxy-2,3-dihydrobenzofuran;
4,6-di-t-butyl-2,2-dibenzyl-5-hydroxy-2,3-dihydrobenzofuran;
4,6-di-t-butyl-2-chloromethyl-5-hydroxy-2,3-dihydrobenzofuran;
4,6-di-t-butyl-5-hydroxy-2,3-dihydrobenzofuran-2-spiro-1'-cyclopentane;
4,6-di-t-butyl-5-hydroxy-2,3-dihydrobenzofuran-2-spiro-1'-cyclohexane;
4,6-di-t-butyl-5-hydroxy-2,3-dihydrobenzofuran-2-spiro-1'-cycloheptane;
4,6-di-t-butyl-5-hydroxy-2,3-dihydrobenzofuran-2-spiro-1'-cyclooctane;
4,6-di-t-butyl-5-hydroxy-2,3-dihydrobenzofuran-2-spiro-4'-tetrahydropyran;
5-hydroxy-4,6-di-t-butyl-2,2-dimethyl-7-propyl-2,3-dihydrobenzofuran;
4,6-di-t-butyl-5-hydroxybenzofuran;
4,6-di-t-butyl-5-hydroxy-2-methylbenzofuran;
2,4,6-tri-t-butyl-5-hydroxybenzofuran;
2,6-di-t-butyl-3-methyl-4-propyloxyphenol;
4-allyloxy-2,6-di-t-butyl-3-methylphenol;
1,3-bis(3,5-di-t-butyl-4-hydroxy-2-methylphenoxy) propane;
4,6-di-t-butyl-2,2-di-n-pentyl-5-hydroxy-2,3-dihydrobenzofuran;
4,6-di-t-butyl-2,2-di-n-octyl-5-hydroxy-2,3-dihydrobenzofuran;
4,6-di-t-butyl-2,2-di-n-heptyl-5-hydroxy-2,3-dihydrobenzofuran;
4,6-di-t-butyl-2,2-di-n-hexyl-5-hydroxy-2,3-dihydrobenzofuran;
2,2-di-i-amyl-4,6-di-t-butyl-5-hydroxy-2,3-dihydrobenzofuran;
4,6-di-t-butyl-5-hydroxy-2-methyl-2-(4,8,12-trimethyltrideca-3(E),7(E),11-trienyl)-2,3-dihydrobenzofuran;
4,6-di-t-butyl-5-hydroxy-2-methyl-2-(4',8',12'-trimethyltridecyl)-2,3-dihydrobenzofuran; and
4,6-di-t-butyl-5-hydroxy-2-(5-hydroxy-4-methyl-3(E)-pentenyl)-2-methyl-2,3-dihydrobenzofuran.

The compounds of general formula (1) used in the present invention can be synthesized according to the procedures described in JPA No. 6-206842/94, for example.

The prophylactic/therapeutic agents for atherosclerosis or xanthomatosis of the present invention can be used as various pharmaceutical compositions containing a compound of general formula (1) as an active ingredient in combination with a physiologically non-toxic solid or liquid pharmaceutical carrier. These pharmaceutical compositions are formulated and used in various dosage forms depending on the administration route to be used. Dosage forms include tablets, granules, pills, capsules, solutions, syrups, suspensions, emulsions and injections. Suitable pharmaceutical carriers include commonly used excipients, binders, disintegrants, lubricants, coating agents, dissolution-aids, emulsifiers, suspending agents, stabilizers and solvents.

The compounds of general formula (1) of the present invention and the pharmaceutical compositions described above can be administered orally or parenterally by such as intravenous injection, or as a sustained-release formulation, or topically by means of a catheter.

The actual dosage of the compounds of general formula (1) required for the prevention or treatment of atherosclerosis or xanthomatosis depends on the age of the patient, severity of condition, administration route or other factors, and an acceptable dosage which is effective is normally 1–1000 mg, preferably 100–300 mg per adult daily. Such dosage is preferably administered to the patient in need of the prevention or treatment in from one to three dose administrations daily.

The following examples further illustrate the present invention, but are not construed as limiting the same.

EXAMPLES

Example 1

4,6-di-t-butyl-2,2-di-n-pentyl-5-hydroxy-2,3-dihydrobenzofuran

The title compound was synthesized by the procedure described in JPA No. 6-206842/94.

Test Example 1

Effect on Atherosclerosis in an in vivo Atherosclerosis Model (1)

In order to evaluate the inhibitory effect of the compound of Example 1 on atherosclerosis in an in vivo atherosclerosis model, Watanabe Heritable Hyperlipidemic (WHHL) rabbits were used.

Specifically, 4 groups of 4 or 5 WHHL rabbits (Kbl: 2 to 3-month-old male) were conditioned for a week, and then 3 groups of them received 1% probucol and 0.2% and 0.5% Example 1 compound contained in a normal chow diet, respectively, by limited feeding (40 g/kg) once a day for 6 months. The other one group similarly received the normal chow diet containing neither probucol nor the compound of Example 1 and was used as a control.

After administration of the compound for 6 months, the aorta was removed from each of the animals and visualized to prepare a photograph of the inside of the aortic sample. White fat deposition area which represents arteriosclerotic lesions was determined by the image analysis on the photograph for each of three parts of the aortic sample (arch, chest and abdomen). From the results, the proportions (percentage) of the fat deposition area to the overall area for the arch section and the whole aorta were obtained. Four or five animals were used for each group for the evaluation.

Table 1 shows the results of the arch section alone which contains the most advanced arteriosclerotic lesions as well as the results of the whole aorta.

TABLE 1

Inhibitory effect on formation of arterioscleortic lesions in WHHL rabbit aortae

| Dosage | Control | Probucol 1% | Compound of Example 1 0.5% | 0.2% |
| --- | --- | --- | --- | --- |
| Number of animals used | 4 | 5 | 5 | 5 |
| Lesions in arch section (%) | 76.7 ± 2.6 | 53.9 ± 5.6* | 52.6 ± 7.4* | 65.7 ± 3.7 |
| Lesions in the whole aorta (%) | 73.1 ± 4.6 | 25.2 ± 2.6** | 37.4 ± 5.7** | 44.3 ± 6.8** |

Means ± standard deviation * $P < 0.05$, ** $P < 0.01$.

As shown in Table 1, the compound of Example 1 exhibits a strong inhibitory effect on the atherosclerosis in WHHL rabbits. The atherosclerosis inhibitory effect is comparable to that of probucol even at a half of the dosage of probucol.

Test Example 2

Effect on Atherosclerosis in an in vivo Atherosclerosis Model (2)

In order to evaluate the inhibitory effect of the compound of Example 1 on atherosclerosis in an in vivo atherosclerosis, LDL receptor-deficient mice were used.

Specifically, 4 groups of 5 to 10 LDL receptor-deficient mice (CSK: 6 week-old male and female) were conditioned for a week, and then 2 groups of them freely received high-fat diets (cholesterol content 1.25%) containing 0.5% probucol and 0.5% Example 1 compound, respectively, for 13 weeks. One of the remaining two groups similarly received a high-fat diet containing neither probucol nor the compound of Example 1 and was used as a control and the other one group similarly received a normal, chow diet containing neither probucol nor the compound of Example 1.

After administration of the compound for 13 weeks, the arcus aorta was removed from each of the animals, transversely sectioned and stained with Sudan IV. The area of arteriosclerotic lesions was determined by an image analysis under an optical microscope. The average of the area of arteriosclerotic lesions in the aucus aortae was calculated for each animal. The number of animals used for the evaluation was 5 for the normal chow diet group consisting of female mice and 7–9 for the other groups.

Table 2 shows the results of the determination of the area of arteriosclerotic lesions.

TABLE 2

Inhibitory effect on formation of arteriosclerotic lesions in LDL receptor-deficient mice

|  | Control | Probucol | Compound of Example 1 | Normal feed |
| --- | --- | --- | --- | --- |
| Number of animals |  |  |  |  |
| (male) | 8 | 8 | 7 | 8 |
| (female) | 9 | 7 | 8 | 5 |
| Area of Arteriosclerotic lesions (mm$^2$) |  |  |  |  |
| male | 0.306± 0.033 | 0.376± 0.045 | 0.185 ± 0.027* | 0.004 ± 0.002** |
| female | 0.270± 0.042 | 0.245± 0.024 | 0.192 ± 0.031 | 0.001 ± 0.001** |

Means ± standard deviation * $P < 0.05$, ** $P < 0.01$.

As shown in Table 2, the compound of Example 1 exhibits an inhibitory effect on arteriosclerosis in LDL receptor-deficient mice. The inhibitory effect is not observed in the antioxidant, probucol.

Test Example 3

Effect on Atherosclerosis in an in vivo Atherosclerosis Model (3)

In order to evaluate the inhibitory effect of the compound of Example 1 on atherosclerosis in an in vivo atherosclerosis model, LDL receptor/apolipoprotein E double hetero-deficient (LDL receptor/Apo E hetero-deficient) mice were used.

Specifically, 4 groups of 5 to 10 LDL receptor Apo E hetero-deficient mice (CSK: 6 week-old female) were conditioned for a week, and then 2 groups of them freely received high-fat diets (cholesterol content 1.25%) containing 0.5% probucol and 0.5% Example 1 compound, respectively, for 6 months. One of the remaining two groups similarly received a high-fat feed containing neither probucol nor the compound of Example 1 and was used as a control and the other one group similarly received a normal, chow diet containing neither probucol nor the compound of Example 1.

After administration of the compound for 6 months, the arcus aorta was removed from each of the animals, transversely sectioned and stained with Sudan IV. The area of arteriosclerotic lesions was determined by an image analysis under an optical microscope. The average of the area of arteriosclerotic lesions in the aucus aortae was calculated for each animal. The number of animals used for the evaluation was 2 for the normal feed group and 5–6 for the other groups.

Table 3 shows the results of the determination of the area of arteriosclerotic lesions.

TABLE 3

Inhibitory effect on formation of arteriosclerotic lesions in LDL receptor/Apo E hetero-deficient mice

|  | Control | Probucol | Compound of Example 1 | Normal feed |
|---|---|---|---|---|
| Number of animals | 5 | 6 | 5 | 2 |
| Area of Arteriosclerotic lesions (mm$^2$) | 0.464± 0.082 | 0.451± 0.052 | 0.150 ± 0.017** | 0.000 ± 0.000** |

Means ± standard deviation ** P < 0.01.

As shown in Table 3, the compound of Example 1 exhibits a strong inhibitory effect on arteriosclerosis in LDL receptor/Apo E hetero-deficient mice. The inhibitory effect is not observed in the antioxidant, probucol.

Test Example 4

Effect on Formation of Xanthoma in an in vivo Xanthoma Model

In order to evaluate the inhibitory effect of the compound of Example 1 on xanthoma in an in vivo xanthoma model, LDL receptor-deficient mice were used.

Specifically, 4 groups of 5 to 10 LDL receptor-deficient mice (CSK: 6 week-old male and female) were conditioned for a week, and then 2 groups of them freely received high-fat diets (cholesterol content 1.25%) containing 0.5% probucol and 0.5% Example 1 compound, respectively, for 13 weeks. One of the remaining two groups similarly received a high-fat feed containing neither probucol nor the compound of Example 1 and was used as a control and the other one group similarly received a normal, chow diet feed containing neither probucol nor the compound of Example 1.

After administration of the compound for 13 weeks, xanthomas were scored in both forefeet and palpebrae based on the appearance thereof and the scores were totalized. The number of animals used for the evaluation was 5 for the normal feed group consisting of female mice and 7–9 for the other groups.

Table 4 shows the results the determination of the scores of xanthomas.

TABLE 4

Inhibitory effect on formation of xanthomas in LDL receptor-deficient mice

|  | Control | Probucol | Compound of Example 1 | Normal feed |
|---|---|---|---|---|
| Number of animals |  |  |  |  |
| (male) | 8 | 8 | 7 | 8 |
| (female) | 9 | 7 | 8 | 5 |
| Xanthoma score |  |  |  |  |
| male | 1.13 ± 0.24 | 3.13 ± 0.30** | 0.29 ± 0.20** | 0.0 ± 0.0** |
| female | 2.44 ± 0.24 | 3.43 ± 0.30* | 1.25 ± 0.25** | 0.0 ± 0.0** |

Means ± standard deviation * P < 0.05, ** P < 0.01.

As shown in Table 4, the compound of Example 1 exhibits a strong inhibitory effect on the formation of xanthomas in LDL receptor-deficient mice. The inhibitory effect is not observed in the antioxidant, probucol.

INDUSTRIAL APPLICABILITY OF THE INVENTION

Prophylactic/therapeutic agents for atherosclerosis, xanthomatosis as well as neuroses and cataracts supervening xanthomatosis containing a 2,6-di-t-butylphenol derivative as an active ingredient according to the present invention are useful for the prevention or treatment of atherosclerosis, xanthomatosis as well as neuroses and cataracts supervening xanthomatosis, as demonstrated by the fact that they show a potent inhibitory effect against atherosclerosis in WHHL rabbits, LDL receptor-deficient mice and LDL receptor Apo E double hetero-deficient mice as well as a potent inhibitory effect against xanthomas in LDL receptor-deficient mice.

What is claimed is:

1. A method for treating or preventing artherosclerosis comprising administering to a patient in need thereof an effective amount of a compound of the formula:

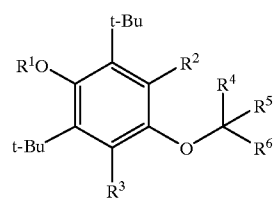

(1)

wherein $R^1$ represents a hydrogen atom, an acyl group or an arylalkoxycarbonyl group;

$R^2$ represents a lower alkyl group;

$R^3$ represents a hydrogen atom or a lower alkyl group; and $R^4$, $R^5$, and $R^6$ may be identical or different and each represents a hydrogen atom, an optionally substituted alkyl group, an optionally substituted alkenyl group, or an optionally substituted alkynyl group, or $R^2$ and $R^4$ together with the oxygen atom may form a furan or dihydrofuran ring, or $R^5$ and $R^6$ may combine to form a cycloalkyl group or a heterosubstituted cycloalkyl group in which one or more methylene groups of the cycloalkyl group are replaced by oxygen, sulfur, or alkyl-substituted nitrogen atoms, provided that $R^6$ is absent when $R^2$ and $R^4$ together with the oxygen form a furan ring, an optically active isomer, or a pharmaceutically acceptable salt thereof.

2. The method according to claim 1 wherein $R^1$ represents a hydrogen atom, an acyl group containing 1 to 10 carbon atoms or an arylalkoxycarbonyl group, the arylalkoxy group of which contains 7 to 11 carbon atoms;

$R^2$ represents an alkyl group containing 1 to 6 carbon atoms;

$R^3$ represents a hydrogen atom or an alkyl group containing 1 to 6 carbon atoms; and $R^4$, $R^5$, and $R^6$ may be identical or different and each represents a hydrogen atom, an optionally substituted alkyl group containing 1 to 20 carbon atoms, an optionally substituted alkenyl group or alkynyl group containing 2 to 20 carbon atoms, or $R^2$ and $R^4$ together with the oxygen atom may form a furan or dihydrofuran ring, or $R^5$ and $R^6$ may combine to form a cycloalkyl group containing 3 to 8 carbon atoms or a heterosubstituted cycloalkyl group in which one or more methylene groups of the cycloalkyl group are replaced by oxygen, sulfur, or C1–6 alkyl-substituted nitrogen atoms.

3. The method according to claim 2 wherein $R^1$ represents a hydrogen atom;

$R^2$ represents an alkyl group containing 1 to 6 carbon atoms;

R3 represents a hydrogen atom or an alkyl group containing 1 to 6 carbon atoms, and $R^4$, $R^5$ and $R^6$ may be identical or different and each represents a hydrogen atom, an optionally substituted alkyl group containing 1 to 10 carbon atoms, an optionally substituted alkenyl or alkynyl group containing 2 to 10 carbon atoms, or $R^2$ and $R^4$ together with the oxygen atom may form a furan or dihydrofuran ring, or $R^5$ and $R^6$ may combine to form a cycloalkyl group containing 5 to 8 carbon atoms or a heterosubstituted cycloalkyl group in which one or more methylene groups of the cycloalkyl group are replaced by oxygen atoms.

4. The method according to claim 3 wherein $R^1$ represents a hydrogen atom, $R^2$ and $R^4$ together with the oxygen atom may form a furan or dihydrofuran ring;

$R^3$ represents hydrogen or and alkyl group containing 1 to 6 carbon atoms, and $R^5$ and $R^6$ may be identical or different and each represents a hydrogen atom, an optionally substituted alkyl group containing 1 to 10 carbon atoms or an optionally substituted alkenyl group containing 2 to 10 carbon atoms, or $R^5$ and $R^6$ may combine to form a cycloalkyl group containing 5 to 8 carbon atoms or a heterosubstituted cycloalkyl group in which one or more methylene groups of the cycloalkyl group are replaced by oxygen atoms.

5. The method according to claim 4 wherein $R^1$ represents a hydrogen atom;

$R^2$ and $R^4$ together with the oxygen atom form a dihydrofuran ring;

$R^3$ represents a hydrogen atom or an alkyl group containing 1 to 6 carbon atoms; and $R^5$ and $R^6$ may be identical or different and each represents a hydrogen atom, an optionally substituted alkyl group containing 1 to 10 carbon atoms, an optionally substituted alkenyl group containing 2 to 10 carbon atoms, or $R^5$ and $R^6$ may combine to form a cycloalkyl group containing 5 to 8 carbon atoms or a heterosubstituted cycloalkyl group in which one or more methylene groups of the cycloalkyl group are replaced by oxygen atoms.

6. The method according to claim 5 wherein the artherosclerosis is selected from the group consisting of coronary artherosclerosis, cerebral artherosclerosis, renal artherosclerosis, artherosclerosis obliterans, diabetic artherosclerosis, and presenile artherosclerosis.

7. The method according to claim 6 wherein the compound is selected is selected from the group consisting of 4,6-di-t-butyl-2,2-di-n-butyl-5-hydroxy-2,3-dihydrobenzofuran;

4,6,di-t-butyl-5-hydroxy-2,3-dihydrobenzofuran-2-spiro-1'-cyclohexane;

4,6-di-t-butyl-5-hydroxy-2,3-dihydrobenzofuran-2-spiro-1'-cycloheptane 4,6,di-t-butyl-5-hydroxy-2,3-dihydrobenzofuran-2-spiro-1'-cyclooctane;

4,6,di-t-butyl-2,2-di-n-pentyl-5-hydroxy-2,3-dihydrobenzofuran; and 2,2-di-iso-amyl-4,6-di-t-butyl-5-hydroxy-2,3-dihydrobenzofuran.

8. The method according to claim 7 wherein the compound is 4,6,di-t-butyl-2,2-di-n-pentyl-5-hydroxy-2,3-dihydrobenzofuran.

* * * * *